United States Patent [19]
Kanai et al.

[11] Patent Number: 5,428,173
[45] Date of Patent: Jun. 27, 1995

[54] PROCESS FOR THE PREPARATION OF AMINOTHIADIAZOLYLACETYL HALIDE DERIVTIVES

[75] Inventors: Takeo Kanai; Akio Imai, both of Ibaraki; Katsuhiko Sato, Chiba; Homare Shinohara; Kazumi Oishi, both of Ibaraki, all of Japan

[73] Assignee: Eisai Chemical Co., Ltd., Ibaraki Prefecture, Japan

[21] Appl. No.: 129,322

[22] Filed: Sep. 30, 1993

[30] Foreign Application Priority Data

Oct. 2, 1992 [JP] Japan .................................. 4-287092
Sep. 20, 1993 [JP] Japan .................................. 5-255269

[51] Int. Cl.⁶ ............................................. C07D 285/08
[52] U.S. Cl. ............................................. 548/128
[58] Field of Search ............................. 548/128, 194

[56] References Cited

FOREIGN PATENT DOCUMENTS 101198 2/1984 European Pat. Off. ............ 548/194
4128277 4/1992 Japan ................................. 548/128

*Primary Examiner*—Robert Gerstl
*Attorney, Agent, or Firm*—Wenderoth, Lind & Ponack

[57] ABSTRACT

A process is provided for the preparation of an aminothiadiazolylacetyl halide derivative represented by the following formula (II):

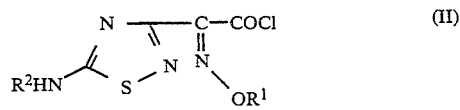

wherein $R^1$ represents a lower alkyl, cycloalkyl or halogenated lower alkyl group; and $R^2$ represents an amino-protecting group or a hydrogen atom, or a salt thereof, which process uses as the starting material a compound represented by the following formula (I):

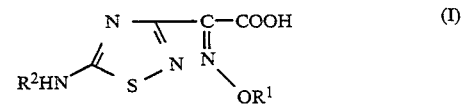

wherein $R^1$ and $R^2$ have the same meanings as defined above, or a salt thereof.

11 Claims, No Drawings

PROCESS FOR THE PREPARATION OF AMINOTHIADIAZOLYLACETYL HALIDE DERIVTIVES

BACKGROUND OF THE INVENTION

1. Field of the Invention

The present invention relates to a process for the preparation of an aminothiadiazolylacetyl halide derivative which is useful as an acylating agent for the preparation of a 7β-acylaminocephalosporin derivative having excellent antimicrobial activities.

2. Description of the Related Art

To improve the antimicrobial activities of cephem compounds, various studies have heretofore been made. It has been found that, among them, chemical modification of the amino group at the 7-position of the cephalosporin skeleton is particularly useful and the formation of a 7-amido linkage with 2-(5-amino-1,2,4-thiadiazol-3-yl)acetic acid leads to a broader antimicrobial spectrum and enhanced antimicrobial activities.

For this purpose, a desired antibiotic having excellent antimicrobial activities can be prepared generally by modifying the carboxyl group of 2-(5-amino-1,2,4-thiadiazol-3-yl)acetic acid to obtain a reactive derivative and then subjecting the derivative to condensation with a corresponding 7-aminocephalosporin derivative. Examples of the reactive derivative at the carboxyl group include acid halides such the acid chloride and acid bromide, the acid anhydride, mixed acid anhydrides, active esters and active acid amides.

Although a number of reactive derivatives at the carboxyl group can be given as referred to above, acid halides such as the acid chloride and acid bromide are employed predominantly from the viewpoints of reactivity, operation efficiency and the like.

2-(5-Amino-1,2,4-thiadiazol-3-yl)acetic acid has in its molecule two active functional groups, that is, an amino group and a carboxyl group. Upon halogenation of the carboxyl group, in general, the other functional group, i.e., the amino group is first blocked with a protecting group such as a t-butoxycarbonyl group (hereinafter referred to as "Boc") and the carboxyl group is then subjected to halogenation.

For instance, Csendes et al. disclosed in Journal of Antibiotics, 36, 1020–1033(1983) a process for the synthesis of a desired antibiotic. According to the process, a mixture of oxalyl chloride and N,N-dimethylformamide (the so-called Vilsmeier reagent) is added dropwise at −10° C. to a solution of 2-(5-Boc-amino-1,2,4-thiadiazol-3-yl)-2-(Z)-oxyiminoacetic acid in ethyl acetate to convert the acid into acid chloride. Without isolation of the acid chloride a corresponding 7β-aminocephalosporin derivative is added further so that to the acid chloride and the derivative are caused to condense together to yield the desired antibiotic.

In addition, Kamiya, et al. disclose in Japanese Patent Laid-Open No. 156984/1989 another process for the synthesis of a desired antibiotic. According to this process, a liquid mixture of N,N-dimethylformamide and tetrahydrofuran is cooled to −10° C., followed by the addition of phosphorus oxychloride. After stirring the resulting mixture under ice cooling, 2-(5-tritylamino-1,2,4-thiadiazol-3-yl)-2(Z)-fluoromethoxyiminoacetic acid is added at −10° C. to convert it into its acid chloride as in the above-described process. Further, and then, similarly to the process described above, the resulting acid chloride is caused to condense with a corresponding 7β-aminocephalosporin derivative.

Because these processes do not contain any isolation step for the acid chloride, the yield or the like of the aminothiadiazolylacetic acid derivative is not known.

Besides, Sakane et al. disclose in Japanese Patent Laid-Open No. 24389/1982 a further process. According to this process, 2-(5-amino-1,2,4-thiadiazol-3-yl)-2(Z)-ethoxyiminoacetic acid with the amino group being unproteced is chlorinated with phosphorus pentachloride at −20° C. in methylene chloride. Then, the resulting acid chloride is added to diisopropyl ether to precipitate 2-(5-amino-1,2,4-thiadiazol-3-yl)-2-(Z)ethoxyiminoacetyl chloride.hydrochloride in a yield of 89.1%.

An acid halide is, in general, not stable, so that as the above-described Csendes et al. process or that disclosed in Japanese Patent Laid-Open No. 156984/1989, the acid halide tends to be employed for the reaction in the subsequent step without isolation and purification after the formation. The most serious drawback of these processes, however, is that, as the reaction proceeds to the subsequent reaction with the co-existence of reactive by-products formed as a result of the halogenation, these by-products undergo side reactions, leading to additional formation of many by-products. The target acid halide should, therefore, be isolated and purified from the resulting crude products containing many by-products which are relatively similar in structure and physical properties. As a result, the yield of the target acid halide drops substantially and, in some instances, the acid halide cannot have sufficient purity because some of the byproducts cannot be removed no matter what method is employed.

As the process disclosed in Japanese Patent Laid-Open No. 24389/1982, it has been attempted to remove reactive by-products, which resulted from halogenation, as much as possible by once isolating the acid halide. According to the processes which have heretofore been disclosed, the yield of the desired acid halide is low. In addition, the purity of the acid halide is insufficient, because a phosphorus-amide derivative represented by the structural formula (III) described below is by-produced unless the amino group is protected.

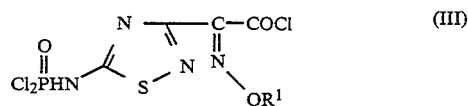
(III)

In addition, the Csendes et al. or Kamiya et al. process, which involves the protection of the amino group, requires an additional step to remove the protecting group, leading to the drawbacks that the yield is reduced due to the need for the additional step and isomerization at the iminoether bond occurs by the use of the acid. Thus, these processes are not satisfactory from the industrial viewpoint.

Even in the processes in which a reactive derivative at the carboxyl group is used instead of an acid halide, problems in reactivity, operation efficiency, safety, cost and the like have remained unsolved. Reactive intermediates produced by the prior art are also dissatisfactory from the viewpoints of purity, stability and the like.

SUMMARY OF THE INVENTION

With a view toward overcoming these drawbacks of the prior art, the present inventors have conducted an extensive investigation. As a result, a process has been found for the preparation of an aminothiadiazolylacetyl halide derivative having high purity and high stability, leading to the completion of the invention.

The present invention therefore provides a process for the preparation of an aminothiadiazolylacetyl halide derivative represented by the following formula (II):

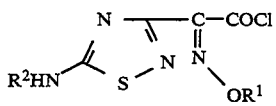

(II)

wherein $R^1$ represents a lower alkyl, cycloalkyl or halogenated lower alkyl group; and $R^2$ represents an amino-protecting group or a hydrogen atom, or a salt thereof, which comprises reacting a compound represented by the following formula (I):

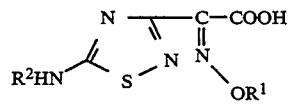

(I)

wherein $R^1$ and $R^2$ have the same meanings as defined above, or a salt thereof with a halogenating reagent or, in the presence of water, with a halogenating agent to form the derivative of the formula (II), pouring the reaction mixture into water and then, isolating the derivative of the formula (II) in a free form from the water or causing the derivative of the formula (II) to precipitate as a hydrogen halide thereof from the reaction mixture, whereby the hydrogen halide is isolated.

According to this process, the compound so obtained has high stability compared with that prepared in a manner known to date so that it can be stored as a material over a long period of time and is therefore extremely useful for industrial purposes.

DETAILED DESCRIPTION OF THE INVENTION AND PREFERRED EMBODIMENT

As the lower alkyl group represented by $R^1$ in the above reaction formula, $C_{1-6}$ lower alkyl groups are preferred. Specific examples include methyl, ethyl, n-propyl, i-propyl, n-butyl, sec-butyl, t-butyl, n-pentyl, sec-pentyl, t-pentyl and n-hexyl groups. Illustrative cycloalkyl groups include cyclopropyl, cyclobutyl, cyclopentyl and cyclohexyl groups. Examples of the halogenated lower alkyl group include the lower alkyl groups exemplified above in which one or more hydrogen atoms have been substituted by the corresponding number of halogen atom(s) such as fluorine, chlorine, bromine and/or iodine atom(s). Specific examples include fluoromethyl, difluoromethyl, trifluoromethyl, 1-fluoroethyl, 2-fluoroethyl, 1,1-difluoroethyl, 1,2-difluoroethyl, 2,2-difluoroethyl, 1,1,1-trifluoroethyl, 1,1,2-trifluoroethyl, 1,2,2-trifluoroethyl, 2,2,2-trifluoroethyl, chloromethyl, dichloromethyl, trichloromethyl, 1-chloroethyl, 2-chloroethyl, 1,1-dichloroethyl, 1,2-dichloroethyl, 2,2-dichloroethyl, 1,1,1-trichloroethyl, 1,1,2-trichloroethyl, 1,2,2-trichloroethyl and 2,2,2-trichloroethyl groups.

In addition, regarding the configuration at the alkoxyimino group or substituted alkoxyl group in the formula (I), there exist a syn-isomer (Z) represented by the following formula (IV):

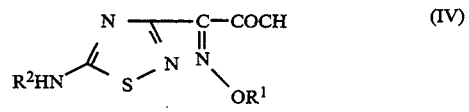

(IV)

and an anti-isomer (E) represented by the following formula (V):

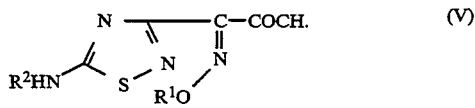

(V)

The present invention includes both the isomers, although the syn-isomer is more preferred from the viewpoint of antimicrobial activities. According to the invention of the present application, use of a raw material [e.g., 2-(5-amino-1,2,4-thiadiazol-3-yl)acetic acid or the like] in its syn-(Z)-isomer makes it possible to obtain the high-purity, target carboxylic acid halide [e.g., 2-(5-amino-1,2,4-thiadiazol-3-yl)acetyl chloride] in its syn-(Z)-form. Such a syn-(Z)-form raw material is therefore very useful.

According to the present invention, the acetyl halide can be obtained without protecting the amino group, that is the other active functional group, in the molecule of 2-(5-amino-1,2,4-thiadiazol-3-yl)acetic acid, although there is no problem even if the amino group is protected. Concerning the protecting group for the amino group represented by $R^2$ in the formula (I), any groups commonly known as amino-protecting ones in organic syntheses can be employed and no limitation is imposed thereon. Specific examples include substituted or unsubstituted alkanoyl groups such as formyl, acetyl, chloroacetyl, dichloroacetyl, propionyl, phenylacetyl, phenoxyacetyl and thienylacetyl groups; substituted or unsubstituted alkoxycarbonyl groups such as methoxycarbonyl, ethoxycarbonyl, phenoxycarbonyl, benzyloxycarbonyl, t-butoxycarbonyl and p-nitrobenzyloxycarbonyl groups; substituted alkyl groups such as methyl, t-butyl, 2,2,2-trichloroethyl, trityl, p-methoxybenzyl, p-nitrobenzyl, diphenylmethyl and pivaloyloxymethyl groups; substituted silyl groups such as trimethylsilyl and t-butyldimethylsilyl groups; and substituted or unsubstituted benzylidene groups such as benzylidene, salicylidene, p-nitrobenzylidene, m-chlorobenzylidene, 3,5-di(t-butyl)-4-hydroxybenzylidene and 3,5-di(t-butyl)benzylidene groups.

These protecting groups, each represented by $R^{2'}$ can be eliminated in a manner known per se in the art such as hydrolysis or reduction, depending on the protecting group employed.

No limitation is imposed on the salt when the compound represented by the formula (I) is used in the form of the salt as a starting material. Examples of the salt include inorganic acid addition salts such as the hydrochloride, sulfate, nitrate, carbonate, bicarbonate, hydrobromate and hydroiodate; organic carboxylic acid addition salts such as the acetate, maleate, lactate, tartrate and trifluoroacetate; organic sulfonic acid addition salts such as the methanesulfonate, hydroxymethanesulfonate, hydroxyethanesulfonate, benzenesulfonate, toluenesulfonate and taurine salt; amine addition salts such as the trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt and phenethylbenzylamine salt; and amino acid addition salts such as the arginine salt, lysine salt, cerin salt, glycine salt, aspartate and glutamate.

The term "halogenating reagent" as used herein means, for example, the Vilsmeier reagent obtained by causing a halogenating agent to act on an acid amide or a phosphoric acid amide. The acid amide can be represented by the following formula (VI):

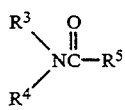 (VI)

wherein $R^3$, $R^4$ and $R^5$ are the same or different and each represents a hydrocarbon group which may contain one or more hydrogen, oxygen, sulfur and/or nitrogen atoms, etc. The term "hydrocarbon group" as used herein means an aliphatic hydrocarbon, aromatic hydrocarbon or the like. The aliphatic hydrocarbon can be either cyclic or acyclic. Examples include lower alkyl, alkenyl, alkinyl, cycloalkyl, cycloalkenyl, cycloalkinyl, aryl and aralkyl groups. These hydrocarbon groups may each be substituted by one or more hydrocarbon, nitro, cyano, alkoxyl, carbonyl, alkoxycarbonyl and/or thiocabonyl groups. Examples of the acid amide (VI) include N,N-dimethylformamide, N-methylformamide, N,N-dimethylacetamide, N-methylacetamide, N-methylbenzamide, acetanilide, N,N-dimethylbenzamide, benzanilide, N-methylpyrrolidone, N-methylformanilide, N-formylpiperidine and N-formylmorpholine, and the like.

The phosphoric acid amide usable in the present invention can be represented by the following formula (VII):

 (VII)

wherein $R^6$ and $R^7$ have the same meanings as $R^3$ and $R^4$ defined above. Specific examples of the phosphoric acid amide (VII) include hexamethylphosphoric acid triamide (HMPA) and hexamethylphosphorous acid triamide (HMPT), and the like.

As the halogenating agent, any one of those ordinarily employed for the synthesis of an acid halide can be used. Examples include phosgene, diphosgene (phosgene dimer), triphosgene (phosgene trimer), thionyl chloride, thionyl bromide, phosphorus trichloride, phosphorus tribromide, phosphorus oxychloride, phosphorus pentachloride, trichloromethyl. chloroformate and oxalyl chloride, and the like.

The reaction using a halogenating reagent, for example, begins with the synthesis of the Vilsmeier reagent, followed by halogenation. The Vilsmeier reagent can be synthesized in a manner known per se in the art. For instance, the reagent is ordinarily prepared by cooling an acid amide or a phosphoric acid amide to $-20°$ to $10°$ C., gradually adding a halogenating agent dropwise to the cooled amide and then reacting them for about 5-60 minutes under stirring. Upon reaction, the acid amide or phosphoric acid amide is generally used in an amount of 1-10 equivalents, preferably 1-5 equivalent, more preferably 1-2.5 equivalents based on the amount of the halogenating agent. A solvent may be used upon preparing the Vilsmeier reagent and/or conducting the halogenation.

Any reaction solvent can be used as long as it does not impair the reaction. Illustrative solvents include tetrahydrofuran, dioxane, methylene chloride, 1,2-dichloroethane, chloroform, carbon tetrachloride, hexane, benzene, toluene, ethyl acetate, butyl acetate, 1,2-dimethoxyethane, N,N-dimethylformamide, N,N-dimethylacetamide, hexamethylphosphoric acid triamide, hexamethylphosphorous acid triamide, dimethylsulfoxide, acetone, acetonitrile and water. These solvents may be used either singly or in combination.

The solvent can be added in an amount of 1-100 volumes, preferably 1-50 volumes, more preferably 1-20 volumes per volume of the raw materials.

The reaction can be carried out generally at $-60°$ C. to the reflux temperature of a reaction solvent, preferably $-30°$ C. to room temperature, more preferably $-20°$ to $10°$ C. Usually, the reaction can be completed in 5 minutes to 48 hours.

When the acid halide is prepared by the reaction with the halogenating agent in the presence of water, the aminothiadiazolylacetyl acid derivative can be used in the form of a hydrate as a starting material. Alternatively, the anhydride of the derivative can also be used after water is added thereto. The hydrate ordinarily contains 0.1–2.0 equivalents of water relative to the aminothiadiazolylacetic acid so that the amount of water added to the anhydride should be adjusted to fall within the above range. Reacting an acid halide with a halogenating agent in the presence of water generally has not been suggested and is a new technique. Moreover, the target product is obtained with excellent yield and purity.

Any halogenating agent can be used as long as it can ordinarily be employed for the synthesis of acid halides. Examples include phosgene, diphosgene (phosgene dimer), triphosgene (phosgene trimer), thionyl chloride, thionyl bromide, phosphorus trichloride, phosphorus tribromide, phosphorus oxychloride, phosphorus pentachloride, trichloromethyl.chloroformate and oxalyl chloride. Upon reaction, the halogenating agent can be used generally in an amount of 1-10, preferably 1-5, more preferably 1-2.5 equivalents relative to the total equivalents of water existing in the aminothiadiazolylacetic acid derivative and the reaction system.

The reaction of the present invention can be conducted either in a solventless manner or in a solvent. In the case where a solvent is employed, any solvent can be used as long as it is inert to the reaction. Preferred examples include tetrahydrofuran, dioxane, 1,3-dioxolan, methylene chloride, 1,2-dichloroethane, chloroform, carbon tetrachloride, n-hexane, benzene, toluene, ethyl acetate, butyl acetate, 1,2-dimethoxyethane, N,N-dimethylformamide, N,N-dimethylacetamide, dimethyl sulfoxide, acetone, acetonitrile and water. These solvents may be used either singly or in combination.

The reaction may ordinarily be conducted at $-40°$ C. to the reflux temperature of the solvent, preferably $-20°$ C. to room temperature, more preferably $-20°$ C. to $10°$ C. The reaction is ordinarily completed in a time ranging from 5 minutes to 48 hours.

After the halogenation is completed, the high-purity acid halide, that is, the target product can be isolated either as a free halide (which is free of any salt) or as a hydrogen halide.

To obtain the acid halide in a free form, crystals of the free halide may be caused to precipitate by pouring the halogenated reaction mixture into water. As disclosed in the Examples of Japanese Patent Laid-Open No. 128277/1992, it was only possible to obtain the target product having a purity of about 60–80% according to the prior art. According to the process of the present invention, however, the acid halide can be obtained in a free form with purity as high as 90%. The free acid halide according to the present invention has excellent stability so that it can be stored for a long period of time. In addition, use of the acid halide for the subsequent step such as amidation of the cephalosporin skeleton, therefore, can obviate the need for its preparation just before its use unlike the conventional process. The product of this invention is, therefore, very advantageous for industrial production. In addition, when the acid halide is brought into contact with water, its pH is about 3–4 so that it can be employed in the subsequent reaction under milder conditions and therefore, its reaction with a rather instable compound containing the cephalosporin skeleton or the like can be conducted under mild conditions. This has made it possible to prevent side reactions and also isomerization. Furthermore, no hydrogen halide is given off during drying step or storage so that the safety of the operation is high and the product according to this invention has extremely low potential danger of corrosion against production equipment and storage containers.

To obtain the acid halide in the form of the hydrogen halide, on the other hand, a solvent in which the target product is sparingly soluble is added to the halogenating reaction mixture, thereby precipitating the hydrogen halide as crystals. No particular limitation is imposed on the solvent employed here insofar as it is an inert solvent to the target product and is sparingly soluble. Examples include isopropyl ether, n-hexane, cyclohexane, isooctane and petroleum ether. The acid halide obtained according to this process has also purity as high as 90% and up and thus is excellent in both purity and stability.

The above reactions can all be conducted using general raw materials (I). When it is desired to obtain still higher purity and yield, the halogenating reaction can be conducted by using, as a raw material, a compound represented by the following formula (I):

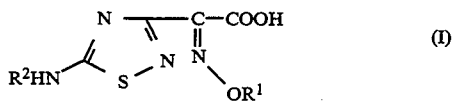

wherein $R^1$ represents a lower alkyl, cycloalkyl or halogenated lower alkyl group; and $R^2$ represents an amino-protecting group or a hydrogen atom, or a salt thereof, said compound or salt having an average particle size not greater than several tens micrometers. As the acid halide can be obtained in an increased yield, the contents of the remaining raw material and by-products decrease, thereby bringing about the advatageous effects that both the yield and the purity can be improved. In this case, a solvent can be used for the reaction even if the raw material (I) has low solubility therein. Use of such an average particle size is therefore very advantageous. To obtain the raw material of such an average particle size, the raw material can be ground by a jet mill or the like in advance. The preparation method of the raw material is however not limited to this method and the raw material obtained by crystallization or the like can also be used. This average particle size is generally 30 μm or smaller, preferably 20 μm or smaller, more preferably 10 μm or smaller.

Any acid halide obtained according to the present invention can be either in the free form or in the form of a hydrogen halide. They have similar reactivity so that it can be used likewise for the subsequent step such as amidation.

To substantiate the above-described advantages of the present invention, some examples of this invention will hereinafter be described. These examples, however, shall not be taken as limiting the scope of the present invention. Incidentally, the purity of each product was determined by adding its sample into methanol, analyzing the resulting solution by high performance liquid chromatography (HPLC) and then calculating the ratio in peak area of the resulting methyl ester derivative to the starting material (I) and any byproducts.

EXAMPLE 1

Synthesis of 2-(5-amino-1,2,4-thiadiazol-3-yl)-2(Z)-methoxyiminoacetyl chloride

In 50.0 ml of tetrahydrofuran (THF), 10.0 g of 2-(5-amino-1,2,4-thiadiazol-3-yl)-2-(Z)-methoxyiminoacetic acid were stirred at −20° C., followed by the dropwise addition of a chlorinating reagent, which had been prepared beforehand by gradually adding 8.4 g of phosphorus oxychloride at 5° C. to a mixture of 20 ml of THF and 4.0 g of N,N-dimethylformamide (DMF) and then reacting them for 30 minutes. After they were reacted for 5 minutes, the reaction mixture was poured into 160 ml of ice water to precipitate crystals. The resulting crystals were collected by filtration, washed with 200 ml of ice water and then dried under reduced pressure, whereby the title compound was obtained. Yield: 9.60 g (88.0%). Purity: 97.2%.

$^1$H NMR (DMSO-$d_6$) δ: 4.12 (3H,s)

Elemental analysis for $C_5H_5N_4O_2SCl$:

Calculated C: 27.22 H: 2.28 N: 25.39

Found C: 27.04 H: 2.25 N: 25.37

IR (KBr), cm$^{-1}$: 3465, 3125, 1779, 1618, 1533, 1403

Further, to confirm that the title compound was the syn-(Z)-isomer with respect to the methoxyimino group, the title compound was converted to 7β-[(Z)-2-(5-amino-1,2,4-thiadiazol-3-yl)2-methoxyiminoacetamido]-3-(4-carbamoylquinuclidinio)methyl-3-cephem-4-acetic acid, a useful antibiotic, by the process disclosed in Japanese Patent Application Laid-Open (Kokai) No. SHO 62-228084. The derivative so obtained was analyzed by $^1$H-NMR, whereby the target compound was confirmed to be the syn-(Z)-isomer.

EXAMPLE 2

Synthesis of 2-(5-amino-1,2,4-thiadiazol-3-yl)-2(Z)-methoxyiminoacetyl chloride

As in Example 1, a reaction mixture was poured into water to precipitate crystals. The resulting crystals were collected by filtration, followed by washing with 200 ml of ice water. The crystals were thereafter suspended in water and the suspension was adjusted to pH 4.8 with a 1M aqueous solution of sodium acetate. The crystals were collected by filtration, followed by stirring for 30 minutes in 120 ml of hexane. After filtration, the filtrate was dried under reduced pressure, whereby the title compound was obtained. Yield: 8.3 g (76.1%). Purity: 94.5%.

Its instrumental analysis data were found to conform with those of Example 1.

EXAMPLE 3

Synthesis of 2-(5-amino-1,2,4-thiadiazol-3-yl)-2-(Z)-methoxyiminoacetyl chloride A reaction mixture was obtained in a similar manner to Example 1 and then, it was poured into water to precipitate crystals. The resulting crystals were collected by filtration, followed by washing with 200 ml of ice water. The crystals were thereafter suspended in water and the suspension was adjusted to pH 4.0 with a 1M aqueous solution of sodium acetate. The resulting solution was extracted with 100 ml of ethyl acetate. The organic layer so obtained was dried over magnesium sulfate, followed by filtration. The filtrate was concentrated and, under reduced pressure, was then dried, whereby a target compound was obtained. Yield: 8.7 g (79.7%). Purity: 97.6%.

Its instrumental analysis data were found to conform with those of Example 1.

EXAMPLE 4

Synthesis of 2-(5-amino-1,2,4-thiadiazol-3-yl)-2(Z]-methoxyiminoacetyl chloride

In 50.0 ml of 1,2-dimethoxyethane (DME), 10.0 g of 2-(5-amino-1,2,4-thiadiazol-3-yl)-2(Z)-methoxyiminoacetic acid were stirred at $-20°$ C., followed by the dropwise addition of a chlorinating reagent, which had been prepared beforehand by gradually adding 8.4 g of phosphorus oxychloride at 5° C. to a mixture of 20 ml of DME and 4.0 g of N,N-dimethylformamide (DMF) and then reacting them for 30 minutes. After they were reacted for 5 minutes, the reaction mixture was poured into 160 ml of ice water to precipitate crystals. The resulting crystals were collected by filtration, washed with 200 ml of ice water and then stirred for 30 minutes in 120 ml of n-hexane. After filtration, the resulting crystals were dried under reduced pressure, whereby the title compound was obtained. Yield: 8.43 g (76.6%). Purity: 97.2%.

Its instrumental analysis data were found to conform with those of Example 1.

EXAMPLE 5

Synthesis of 2-(5-amino-1,2,4-thiadiazol-3-yl)-2(Z)-methoxyiminoacetyl chloride

In 80.0 ml of acetonitrile, 10.0 g of 2-(5-amino-1,2,4-thiadiazol-3-yl)-2(Z)-methoxyiminoacetic acid were stirred at $-20°$ C., followed by the dropwise addition of a chlorinating reagent, which had been prepared beforehand by gradually adding 8.4 g of phosphorus oxychloride at 5° C. to a mixture of 25 ml of acetonitrile and 4.0 g of N,N-dimethylformamide (DMF) and then reacting them for 30 minutes. After they were reacted for 5 minutes, 200 ml of ice water were poured into the reaction mixture to precipitate crystals. The crystals were collected by filtration, washed with 100 ml of ice water and then stirred for 30 minutes in 100 ml of n-hexane. After filtration, the resulting crystals were dried under reduced pressure, whereby the title compound was obtained. Yield: 8.90 g (81.6%). Purity: 97.9%.

Its instrumental analysis data were found to conform with those of Example 1.

EXAMPLE 6

Synthesis of 2-(5-amino-1,2,4-thiadiazol-3-yl)-2(Z)-methoxyiminoacetyl chloride

In 30.0 ml of tetrahydrofuran (THF), 10.0 g of 2-(5-amino-1,2,4-thiadiazol-3-yl)-2(Z)-methoxyiminoacetic acid were stirred at $-20°$ C., followed by the dropwise addition of a chlorinating reagent, which had been prepared beforehand by gradually adding 6.97 g of oxalyl chloride at 5° C. to a mixture of 100 ml of THF and 4.0 g of N,N-dimethylformamide (DMF) and then reacting them for 30 minutes. After they were reacted for 5 minutes, the reaction mixture was poured into 250 ml of ice water to precipitate crystals. The crystals were collected by filtration and washed with 100 ml of ice water. The resulting crystals were thereafter suspended in water and the suspension was adjusted to pH 4.0 with a 1M aqueous solution of sodium acetate. The resulting solution was extracted with 250 ml of ethyl acetate. The organic layer was dried over magnesium sulfate, followed by filtration. The filtrate was concentrated and, under reduced pressure, was then dried, whereby the title compound was obtained. Yield: 7.5 g (68.7%). Purity: 98.7%.

Its instrumental analysis data were found to conform with those of Example 1.

EXAMPLE 7

Synthesis of 2-(5-amino-1,2,4-thiadiazol-3-yl)-2(Z)-methoxyiminoacetyl chloride

In 30.0 ml of 1,2-dimethoxyethane (DME), 10.0 g of 2-(5-amino-1,2,4-thiadiazol-3-yl)-2(Z)-methoxyiminoacetic acid were stirred at $-20°$ C., followed by the dropwise addition of a chlorinating reagent, which had been prepared beforehand by gradually adding 6.97 g of oxalyl chloride at 5° C. to a mixture of 100 ml of DME and 4.0 g of N,N-dimethylformamide (DMF) and then reacting them for 30 minutes. After they were reacted for 5 minutes, the reaction mixture was poured into 200 ml of ice water to precipitate crystals. The crystals were collected by filtration, washed with 100 ml of ice water, collected by filtration and then, stirred for 30 minutes in 100 ml of n-hexane. After filtration, the resulting crystals were dried under reduced pressure, whereby the title compound was obtained. Yield: 8.2 g (75.1%). Purity: 94.1%.

Its instrumental analysis data were found to conform with those of Example 1.

EXAMPLE 8

Synthesis of 2-(5-amino-1,2,4-thiadiazol-3-yl)-2(Z)-methoxyiminoacetyl chloride

In 30.0 ml of tetrahydrofuran (THF), 10.0 g of 2-(5-amino-1,2,4-thiadiazol-3-yl)-2(Z)-methoxyiminoacetic acid were stirred at $-20°$ C., followed by the dropwise addition of a chlorinating reagent, which had been prepared beforehand by gradually adding 5.43 g of trichloromethyl chloroformate at 5° C. to a mixture of 80 ml of THF and 4.0 g of N,N-dimethylformamide (DMF) and then reacting them for 30 minutes. After they were reacted for 5 minutes, the reaction mixture was poured into 200 ml of ice water to precipitate crystals. The crystals were collected by filtration, washed with 100 ml of ice water, collected by filtration, and then stirred for 30 minutes in 100 ml of n-hexane. After filtration, the resulting crystals were dried under reduced pressure, whereby the title compound was obtained. Yield: 9.2 g (84.3%). Purity: 96.5%.

Its instrumental analysis data were found to conform with those of Example 1.

EXAMPLE 9

Synthesis of
2-(5-amino-1,2,4-thiadiazol-3-yl)-2(Z)-fluoromethoxyiminoacetyl chloride In 30.0 ml of tetrahydrofuran (THF), 10.0 g (45.42 mmol) of 2-(5-amino-1,2,4-thiadiazol-3-yl)-2(Z)fluoromethoxyiminoacetic acid were stirred at room temperature to completely dissolve the latter in the former, followed by cooling to −12° C. Added dropwise to the reaction mixture was a chlorinating reagent, which had been prepared beforehand by gradually adding 7.65 g (49.89 mmol) of phosphorus oxychloride at 5° C. into a mixture of 20 ml of THF and 3.7 g (49.93 mmol) of N,N-dimethylformamide (DMF) and then reacting them for 30 minutes. Subsequent to their reaction for 60 minutes with the temperature maintained at −15° C., the reaction mixture was poured into 150 ml of ice water and was then stirred for 20 minutes to precipitate crystals. The crystals were collected by filtration, washed twice with 15 ml aliquots of ice water and then, under reduced pressure, dried, whereby the title compound was obtained. Yield: 8.50 g (77.9%). Purity: 95.7%.

$^1$H NMR (DMSO-d$_6$), δ: 5.84(2H,d,J=5.4 Hz)

Elemental analysis for C$_5$FH$_4$N$_4$O$_2$SCl:
Calculated C: 25.17 H: 1.69 N: 23.48
Found C: 25.21 H: 1.74 N: 23.40

IR (KBr): 3493, 3103, 1802, 1621, 1521, 1454, 1413 cm$^{-1}$

EXAMPLE 10

Synthesis of
2-(5-amino-1,2,4-thiadiazol-3-yl)-2(Z)-fluoromethoxyiminoacetyl chloride In 30.0 ml of tetrahydrofuran (THF), 11.0 g of 2-(5-amino-1,2,4-thiadiazol-3-yl)-2(Z)-fluoromethoxyiminoacetic acid were stirred at −20° C., followed by the dropwise addition of a chlorinating reagent, which had been prepared beforehand by gradually adding 6.97 g of oxalyl chloride at 5° C. to a mixture of 80 ml of THF and 4.0 g of N,N-dimethylformamide (DMF) and then reacting them for 30 minutes. After they were reacted for 5 minutes, the reaction mixture was poured into 400 ml of ice water to precipitate crystals. The crystals were collected by filtration, washed with 100 ml of ice water, and then stirred for 30 minutes in 100 ml of n-hexane. After filtration, the resulting crystals were dried under reduced pressure, whereby the title compound was obtained. Yield: 6.70 g (56.3%). Purity: 91.5%.

Its instrumental analysis data were found to conform with those of Example 9.

Effect Test 1

<Comparison in stability>

To determine the stability of 2-(5-amino-1,2,4-thiadiazol-3-yl)-2(Z)-methoxyiminoacetyl chloride synthesized in Example 1, the stability was measured at a storage temperature of 25° C. and 40° C. along with that of 2-(5-amino-1,2,4-thiadiazol-3-yl)-2(Z)-methoxyiminoacetyl chloride hydrochloride which, as a control produced by a conventional process, had been prepared according to the process described in Journal of Antibiotics, 37, 557–571(1984). Described specifically, each sample to be measured was added to methanol to convert 2-(5-amino-1,2,4-thiadiazol-3-yl)-2(Z)-methoxyiminoacetyl chloride to the ester compound, and the percentage of the free carboxylic acid formed through decomposition during the storage [—COOH/(—COOMe+—COOH)%] was determined using HPLC. In the table shown below, 2-(5-amino-1,2,4-thiadiazol-3-yl)-2(Z)-methoxyiminoacetyl chloride according to the present invention, which was free of any salt form, is indicated as "free acid" whereas 2-(5-amino-1,2,4-thiadiazol-3-yl)-2(Z)-methoxyiminoacetyl chloride hydrochloride is indicated as "hydrochloride".

TABLE 1

| | Stability of acid chloride | | | |
|---|---|---|---|---|
| TMP. Period (days) | Example 1 (free acid) 25° C. | Control (hydrochloride) 25° C. | Example 1 (free acid) 40° C. | Control (hydrochloride) 40° C. |
| 0 | 4.1% | 0.7% | 4.1% | 0.7% |
| 1 | 4.7% | 1.6% | 5.3% | 2.2% |
| 2 | 5.0% | 1.8% | 5.4% | 3.3% |
| 3 | 4.9% | 1.8% | 6.2% | 4.7% |
| 6 | 5.0% | 2.1% | 5.7% | 8.7% |
| 7 | 4.6% | 2.1% | 5.7% | 13.6% |

As can be seen from Table 1, it has been found that compared with the conventional process, the process of the present invention can provide more stable compounds.

Preparation Example 1

Process for the synthesis of
2-(5-amino-1,2,4-thiadiazol-3-yl)-2-fluoromethoxyiminoacetyl anhydride and its hydrate 2-(5-Amino-1,2,4-thiadiazol-3-yl)-2-fluoromethoxyiminoacetic acid which had been synthesized according to the process disclosed in Japanese Patent Laid-Open No. 308287/1989 was dried under heat, whereby its anhydride was obtained.

The resulting anhydride was dissolved in 140 ml of water under stirring. Needle crystals so precipitated were collected by filtration and dried at 40° C. in a vacuum, whereby 2-(5-amino-1,2,4-thiazol-3-yl)-2-fluoromethoxyiminoacetic acid hydrate (water content: 4.65%) was obtained.

EXAMPLE 11

Synthesis of
2-(5-amino-1,2,4-thiadiazol-3-yl)-2-fluoromethoxyiminoacetyl chloride . hydrochloride In 50 ml of methylene chloride, 10.0 g (0.044 mol) of 2-(5-amino-1,2,4-thiadiazol-3-yl)-2-fluoromethoxyiminoacetic acid hydrate were suspended, followed by the addition of 13.3 g (0.064 mol) of phosphorus pentachloride at −20° C. After stirring for 30 minutes, 100 ml of isopropyl ether were added dropwise to the reaction mixture to precipitate crystals. The resulting crystals were collected by filtration, washed with 20 ml of isopropyl ether and then dried, whereby 9.33 g of a title compound were obtained (yield: 77%, purity: 89.7%).

Melting point: 173°–175° C.

$^1$H NMR (DMSO-$d_6$), δ: 3.87(3H,s), 5.78(1H,s), 5.91(1H,s), 8.24(2H,br)

Elemental analysis for $C_6FH_7N_4O_3S$:
Calculated C: 30.77 H: 3.01 N: 23.92
Found C: 30.93 H: 2.89 N: 24.21

The title compound was converted into the methyl ester, on which the following analysis was conducted. Further, the methyl ester was subjected to an x-ray structural analysis, whereby the title compound was found to be the syn-(Z)-isomer with respect to the methoxyimino group [Bull. Chem. Soc. Japan, 66, 2335–2338 (1993)].

<Identification of by-product>

The by-product obtained in the above reaction was converted into the methyl ester as described above and the resulting methyl ester was fractionated and purified by HPLC. As a result of analyses for its identification, the below-described results were obtained. The by-product was therefore found to be the methyl ester of a phosphorus-amide derivative represented by the above formula (IV) in which $R^2$ is a phospholino group [—PO(OH)$_2$]. The methyl ester is therefore represented by the following formula:

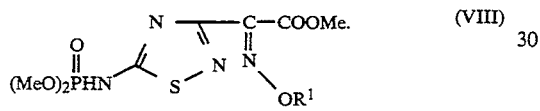

(VIII)

Melting point: 119°–122° C.

$^1$H NMR (DMSO-$d_6$), δ: 3.73(3H,s), 3.76(3H,s), 3.90(3H,s), 5.80(1H,s), 5.92(1H,s), 11.35(1H,br)

Elemental analysis for $C_8FH_{12}N_4O_6PS$:
Calculated C: 28.07 H: 3.54 N: 16.37
Found C: 28.37 H: 3.37 N: 16.68

Mass spectrometric analysis: M+1=343

EXAMPLE 12

Synthesis of 2-(5-amino-1,2,4-thiazol-3-yl)-2-fluoromethoxyiminoacetyl chloride . hydrochloride In 10 ml of methylene chloride, 10 g of 2-(5-amino-1,2,4-thiadiazol-3-yl)-2-fluoromethoxyiminoacetic acid were suspended, followed by the addition of 0.2 ml of water. The reaction mixture was cooled to −20° C., to which 11.88 g of phosphorus pentachloride were gradually added. The resulting mixture was stirred for 30 minutes. The reaction mixture was thereafter added dropwise to a mixed solution of 120 ml of isopropyl ether and 32 ml of iso-octane to precipitate crystals. The resulting crystals were collected by filtration, washed with 20 ml of isopropyl ether and then dried, whereby 11.2 g of a title compound were obtained (yield: 89.6%, purity: 95.5%).

Its instrumental analysis data were found to conform with those of Example 11.

Effect Test 2

<Comparison in purity>

Effects of the water addition for the purity improvement of the target compound are shown in Table 2. As an illustrative hydrate, the sample obtained in Example 11 was used and as a non-hydrated example, the sample obtained as in Example 11 except for the omission of water was used.

TABLE 2

| Effects of water addition | | Anhydride | Hydrate |
|---|---|---|---|
| Acid halide | | 88.26% | 96.15% |
| Byproduct | Carboxylic acid | 5.73% | 0.98% |
| | Phosphorus-amide derivative | 4.03% | 1.38% |
| | Anti-isomer | 0.67% | 0.68% |

In the above table, "carboxylic acid" means 2-(5-amino-1,2,4-thiazol-3-yl)-2-fluoromethoxyiminoacetic acid; "anti-isomer" a geometric isomer at the hydroxyimino portion, that is, the isomer in the above formula (V); "phosphorus-amide derivative" a compound represented by the above formula (III) in which $R^1$ represents a fluoromethyl group and $R^2$ represents a hydrogen atom; and "acid halide" 2-(5-amino-1,2,4-thiadiazol-3-yl)-2-fluoromethoxyiminoacetyl chloride, respectively.

As can be seen from Table 2, aminothiadiazolylacetyl halides derivative having high purity and high industrial utility can be obtained according to the present invention.

Effect Test 3

<Effects of the particle size of raw material>

To investigate any influence of the particle size to the reaction, the following experiment was carried out. The results are presented in Table 3.

EXAMPLE 13

Synthesis of 2-(5-amino-1,2,4-thiadiazol-3-yl)-2-(Z)-methoxyiminoacetyl chloride In a manner similar to Example 1, a reaction was conducted using 2-(5-amino-1,2,4-thiadiazol-3-yl)-2-(Z)-methoxyiminoacetic acid whose average particle size was 2.4 μ. Subsequent to dropwise addition of a chlorinating reagent which had been prepared from phosphorus oxychloride and N,N-dimethylformamide, they were reacted for 1 minute. The reaction product was post-treated, and its purity was analyzed by HPLC by the method described above.

EXAMPLE 14

Synthesis of 2-(5-amino-1,2,4-thiadiazol-3-yl)-2-(Z)-methoxyiminoacetyl chloride)

In a manner similar to Example 13, a reaction was conducted using 2-(5-amino-1,2,4-thiadiazol-3-yl)-2-(Z)-methoxyiminoacetic acid whose average particle size was 64.5 μ. Subsequent to dropwise addition of the chlorinating reagent, they were reacted for 40 minutes. The reaction product was post-treated, and its purity was analyzed by HPLC by the method described above.

TABLE 3

| Effects of the particle size of raw material | | | |
|---|---|---|---|
| Average particle size (μ) | Target product | Byproducts | Remaining raw material |
| 2.4 | 95.0% | 0.5% | 4.0% |

TABLE 3-continued

| Effects of the particle size of raw material | | | |
|---|---|---|---|
| Average particle size (μ) | Target product | Byproducts | Remaining raw material |
| 64.5 | 75.0% | 3.0% | 21.0% |

In the above table, the "target product" means 2-(5-amino-1,2,4-thiadiazol-3-yl)-2-(Z)-flouoromethoxyiminoacetyl chloride, the "byproducts" the reaction product with phosphorus oxychloride, said reaction product being represented by the formula (IV) in which $R^2$ is a phospholino group [—PO(OH)$_2$], and an anti-isomer thereof, and the "raw material" 2-(5-amino-1,2,4-thiadiazol-3-yl)-2-(Z)-flouoromethoxyiminoacetic acid. The term "remaining raw material" indicate the raw material still remaining after the reaction.

As is apparent from Table 3, control of the average particle size of the raw material to 30 μ or smaller makes it possible to obtain its corresponding aminothiadiazolylacetyl chloride derivative with high purity in a high yield.

We claim:

1. A process for the preparation of an aminothiadiazolylacetyl halide derivative represented by the following formula (II):

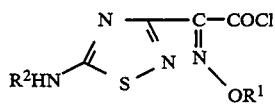
(II)

wherein $R^1$ represents a lower alkyl, cycloalkyl or halogenated lower alkyl group; and $R^2$ represents an amino-protecting group or a hydrogen atom, which comprises reacting a compound represented by the following formula (I):

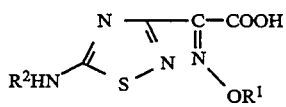
(I)

wherein $R^1$ and $R^2$ have the same meanings as defined above, or a salt thereof with a halogenating reagent to form the derivative of the formula (II), pouring the reaction mixture into water and then, isolating the derivative of the formula (II) in free form from the water.

2. A process of claim 1, wherein a halogenating reagent is a mixture of an acid amide or phosphoric acid amide and a halogenating agent.

3. A process of claim 1, wherein the halogenating reagent is a mixture of N,N-dimethylformamide and phosphorus oxychloride.

4. A process of claim 1, wherein the halogenating agent to be used in the presence of water is phosphorus pentachloride.

5. A process of claim 1, wherein $R^1$ represents a methyl group.

6. A process of claim 1, wherein $R^1$ represents a fluoromethyl group.

7. A process of claim 1, wherein the compound represented by the formula (I) or the salt thereof to be used has an average particle size less than 30 micron.

8. A process of any one of claim 1, wherein the compound represented by the formula (I) or the salt thereof to be used has an average particle size less than 10 micron.

9. A process for the preparation of an aminothiadiazolylacetyl halide derivative represented by the following formula (II):

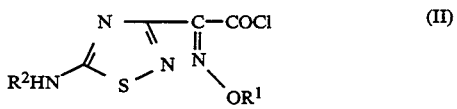
(II)

wherein $R^1$ represents a lower alkyl, cycloalkyl or halogenated lower alkyl group; and $R^2$ represents an amino-protecting group or a hydrogen atom, which comprises reacting a compound represented by the following formula (I):

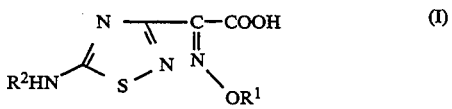
(I)

wherein $R^1$ and $R^2$ have the same meanings as defined above, or a salt thereof in the presence of water, with a halogenating agent to form the derivative of the formula (II), pouring the reaction mixture into water and then, isolating the derivative of the formula (II) in free form from the water.

10. A process of claim 9, wherein the compound represented by the formula (I) or the salt thereof is a hydrate.

11. A process for the preparation of a hydrogen halide of an aminothiadiazolylacetyl halide derivative represented by the following formula (II):

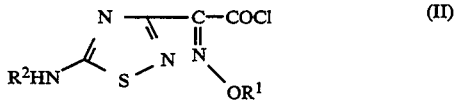
(II)

wherein $R^1$ represents a lower alkyl, cycloalkyl or halogenated lower alkyl group; and $R^2$ represents an amino-protecting group or a hydrogen atom, which comprises reacting a compound represented by the following formula (I):

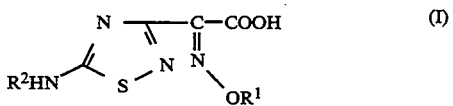
(I)

wherein $R^1$ and $R^2$ have the same meanings as defined above, or a salt thereof in the presence of water, with a halogenating agent to form the derivative of the formula (II), causing the derivative of the formula (II) to precipitate for isolation as the hydrogen halide thereof from the reaction mixture by the addition of a solvent in which the target product is sparingly soluble.

* * * * *